(12) United States Patent
Zacco

(10) Patent No.: US 6,619,290 B1
(45) Date of Patent: Sep. 16, 2003

(54) MOUTHPIECE FOR REDUCING SNORING

(76) Inventor: Christopher B. Zacco, 1217 SE. 7th St., Ocala, FL (US) 34471

( * ) Notice: Subject to any disclaimer, the term of this patent is extended or adjusted under 35 U.S.C. 154(b) by 0 days.

(21) Appl. No.: 10/289,588

(22) Filed: Nov. 7, 2002

(51) Int. Cl.[7] ................................................. A61F 5/56
(52) U.S. Cl. ...................... 128/848; 128/859; 128/861; 128/862; 602/902
(58) Field of Search ................................ 128/846, 848, 128/859–862; 602/902

(56) References Cited

U.S. PATENT DOCUMENTS

| 4,901,737 A | 2/1990 | Toone |
| RE33,442 E | 11/1990 | George |
| 5,046,512 A | 9/1991 | Murchie |
| 5,365,945 A | 11/1994 | Halstrom |
| 5,467,783 A | 11/1995 | Meade |
| 5,536,168 A | 7/1996 | Bourke |
| 5,570,704 A | 11/1996 | Buzzard et al. |
| 5,683,244 A | 11/1997 | Truax |
| 5,868,138 A | 2/1999 | Halstrom |
| 5,899,691 A | 5/1999 | Parker et al. |
| 6,161,542 A | 12/2000 | Halstrom |
| 6,170,485 B1 | 1/2001 | Orrico |
| 6,302,110 B1 | 10/2001 | Yoshida |
| 6,408,851 B1 | 6/2002 | Karell |

*Primary Examiner*—Michael A. Brown
(74) *Attorney, Agent, or Firm*—Allen, Dyer, Doppelt, Milbrath & Gilchrist, P.A.

(57) ABSTRACT

A mouthpiece and method for reducing snoring comprise a mouthpiece body of a thermoplastic material having a shape generally complementary to the person's dental arch, including a posterior end having two spaced apart members positioned toward the back of the person's dental arch when properly worn, and an anterior end having an airway opening therethrough, the anterior end positioned when properly worn to support the person's lips spaced apart so that air flows through the airway opening; and a substantially rigid, removable protective mold of a thermostable material, said protective mold complementary to said mouthpiece body and separably engaged therewith so that the mold protects at least lower and lateral peripheries of the mouthpiece body.

8 Claims, 8 Drawing Sheets

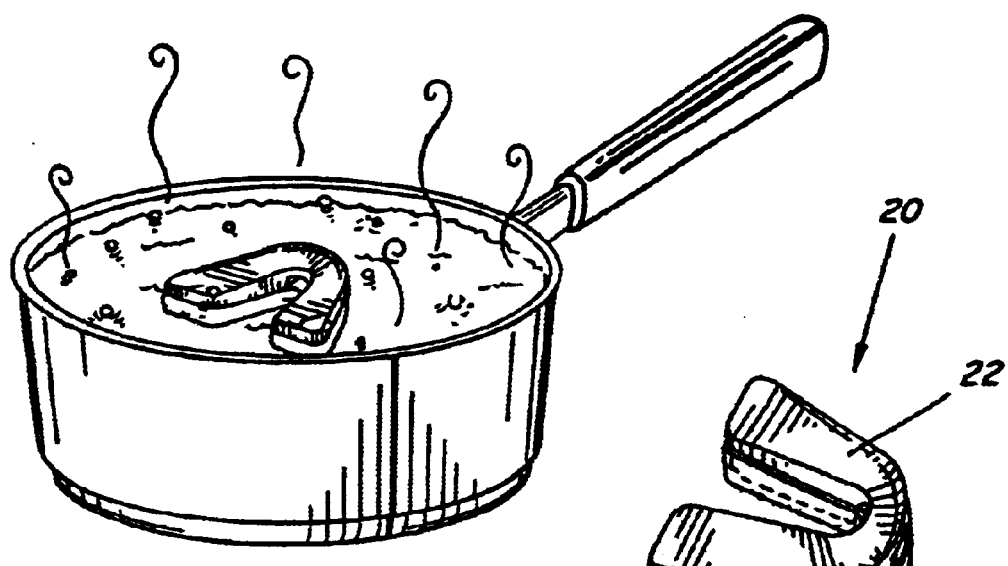
FIG. 6A.
FIG. 6B.
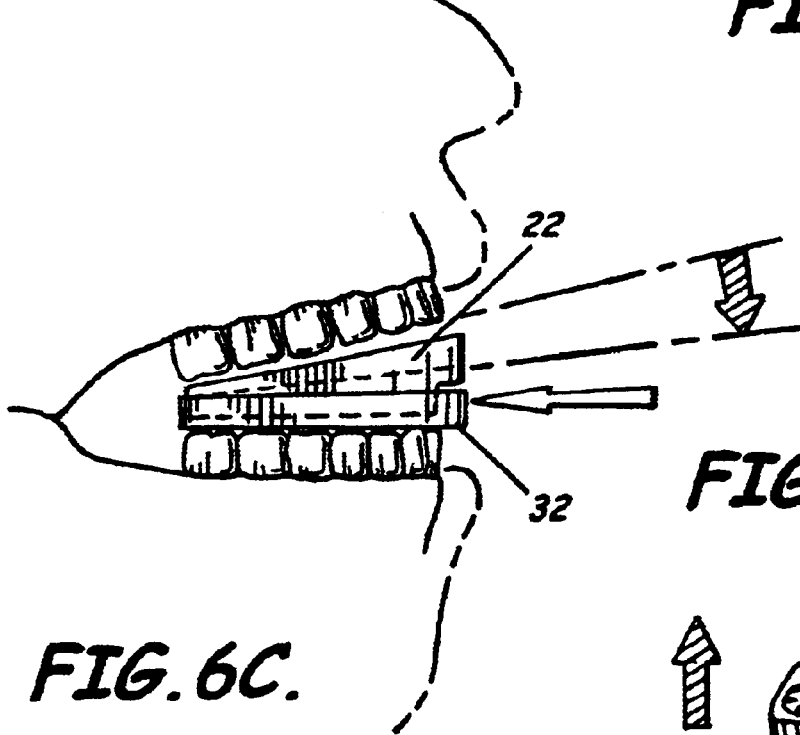
FIG. 6C.
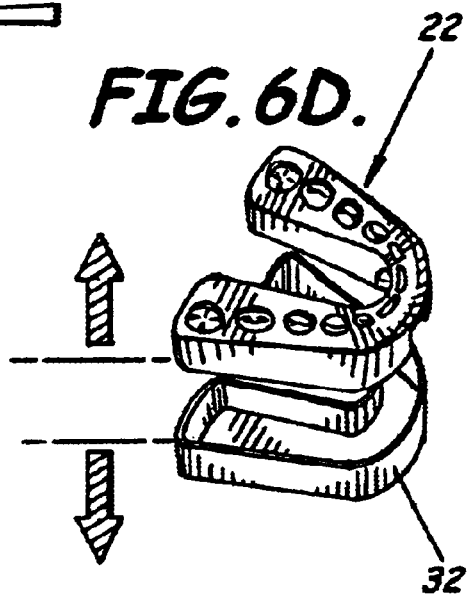
FIG. 6D.

MOUTHPIECE FOR REDUCING SNORING

FIELD OF THE INVENTION

The present invention relates to the field of sleep aids and, more particularly, to a thermoplastic mouthpiece for helping to reduce snoring in a wearer.

BACKGROUND OF THE INVENTION

It is well known that many people snore when asleep. Snoring is an unconscious activity which is often not even noticed by the person who snores, but is typically quite bothersome to those sleeping nearby.

Medical references define snoring as a rough, rattling, inspiratory noise generally produced by vibration of the pendulous palate, or sometimes by the vocal cords, during sleep. Snoring may be produced as a rale, especially a whistling or sonorous rale produced in the larger bronchi or the trachea. This condition is caused by some narrowing of the upper airway passages, such that when the person is asleep, the airflow is somewhat obstructed and must be forced.

SUMMARY OF THE INVENTION

With the foregoing in mind, the present invention advantageously provides a thermoplastic mouthpiece which may be custom fitted directly by the user to conform to his or her natural dental arch. The mouthpiece is reusable, but intended to be disposable at the user's discretion. The thermoplastic mouthpiece includes an opening at an anterior portion of the mouthpiece, the portion which keeps the wearer's lips spaced apart when the mouthpiece is properly worn in the mouth. With the lips slightly apart, the anterior opening allows free airflow in and out of the wearer's mouth, thereby helping to reduce snoring.

In use, the wearer heats the thermoplastic mouthpiece until it softens sufficiently for biting down on the mouthpiece to imprint the wearer's teeth pattern thereon. The mouthpiece includes a protective mold along a lower surface, the mold extending upwardly to also protect lateral surfaces of the mouthpiece. The protective mold is thermostable and does not soften when the mouthpiece is heated, which is preferably accomplished by placing the mouthpiece in a hot water bath for a few minutes. When the mouthpiece softens and cools a bit, the wearer inserts the device into the mouth such that it is substantially aligned with the dental arch, and gently bites down on the mouthpiece to thereon make an impression with his teeth. Of course, along the lower surface of the mouthpiece the protective mold prevents the teeth from leaving an imprint. This helps maintain a proper angle of inclination between the spaced apart lower and upper surfaces of the mouthpiece, and it is this angle which is most helpful in keeping the wearer's lips apart during sleep, and thus help the airway to stay open. Once the mouthpiece has been imprinted, the wearer removes the protective mold and inserts the mouthpiece into his mouth when preparing for sleep.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which:

FIGS. 6A–6D illustrates various aspects of a method of the present invention;

DETAILED DESCRIPTION OF THE PREFERRED EMBODIMENT

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art.

Figure 1:
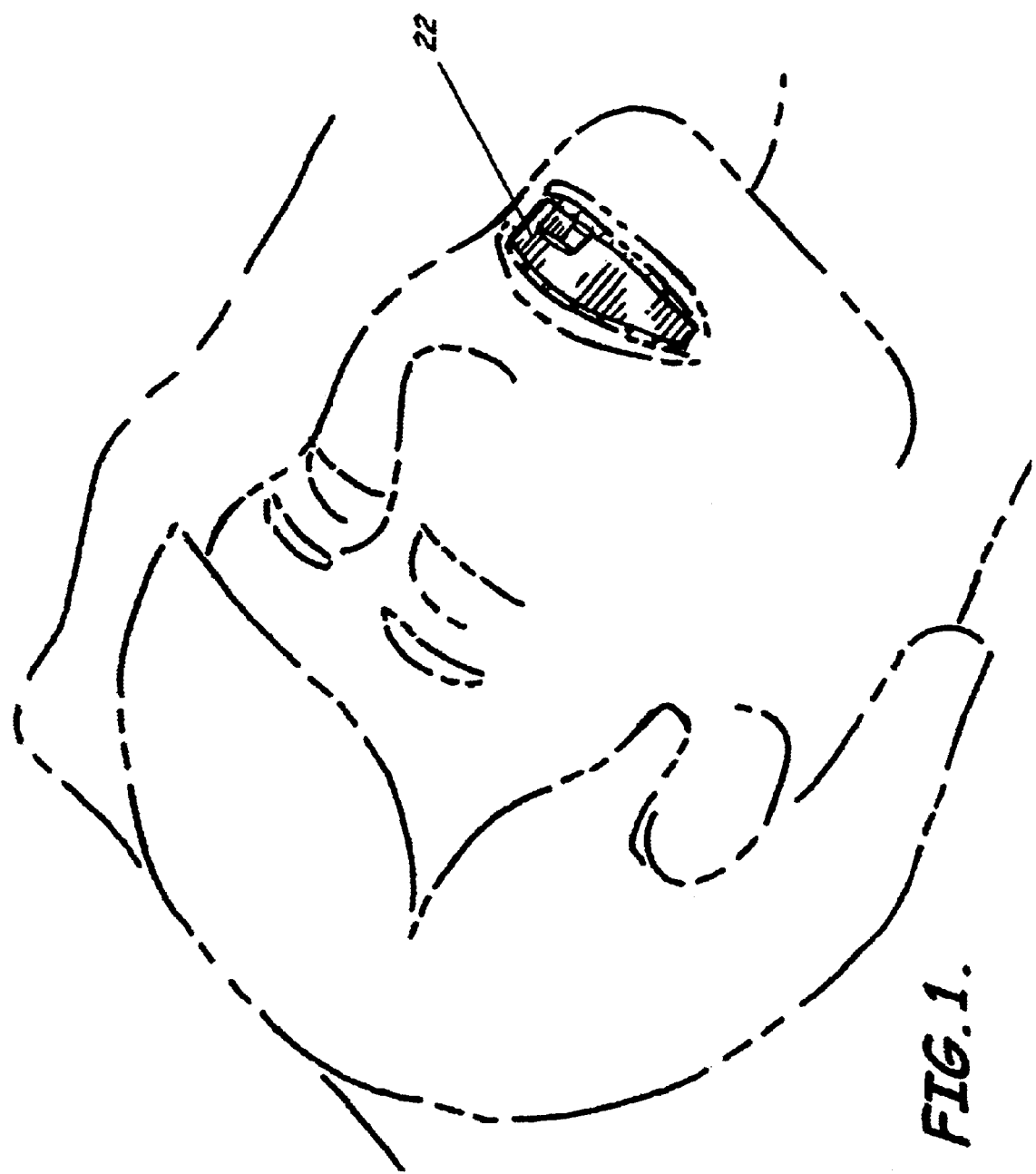
FIG. 1 shows an overall view of a sleeper wearing the mouthpiece according to an embodiment of the present invention.
Figure 2:
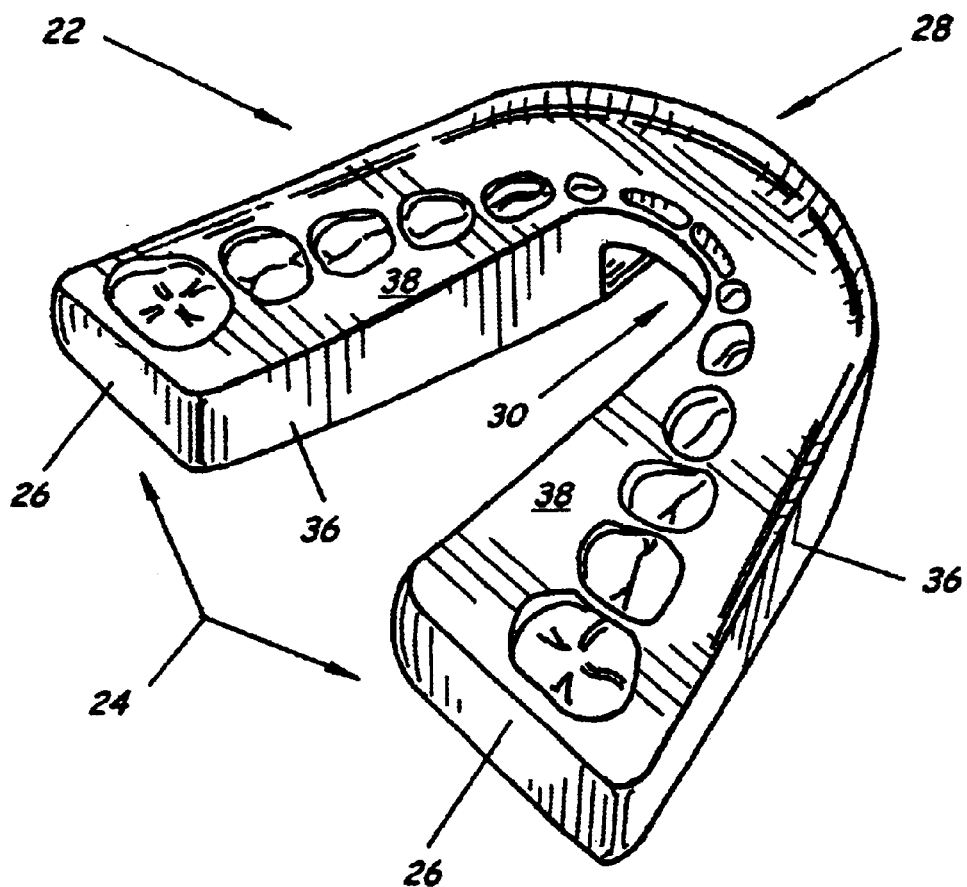
FIG. 2 is a top perspective view of the mouthpiece of FIG. 1.

FIGS. 1–12 illustrate the various aspects of the inventive mouthpiece herein described. The invention discloses a mouthpiece 20 for use by a person during sleep to aid in reducing snoring. The mouthpiece 20 comprises a mouthpiece body 22 made of a thermoplastic material having a shape generally complementary to the person's dental arch, including a posterior end 24 having two spaced apart members 26 positioned toward the back of the person's dental arch when properly worn, and an anterior end 28 having an airway opening 30 therethrough, the anterior end positioned when properly worn to support the person's lips spaced apart, as shown in FIG. 1, so that air flows through the airway opening. The mouthpiece 20 additionally includes a substantially rigid protective mold 32 made of a thermostable material, said protective mold being complementary to said mouthpiece body 22 and removably engaged therewith so that the mold protects at least lower 34 and lateral 36 surfaces of the mouthpiece body, as illustrated in FIGS. 6A–6D.

Figure 3:
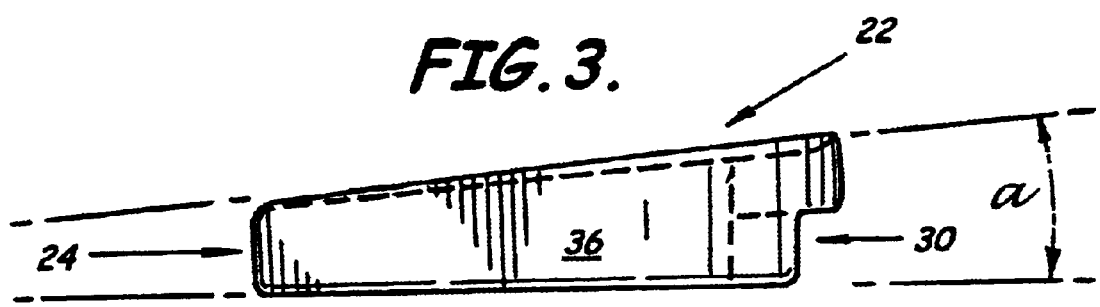
FIG. 3 shows a side elevation of the present mouthpiece.
Figure 4:
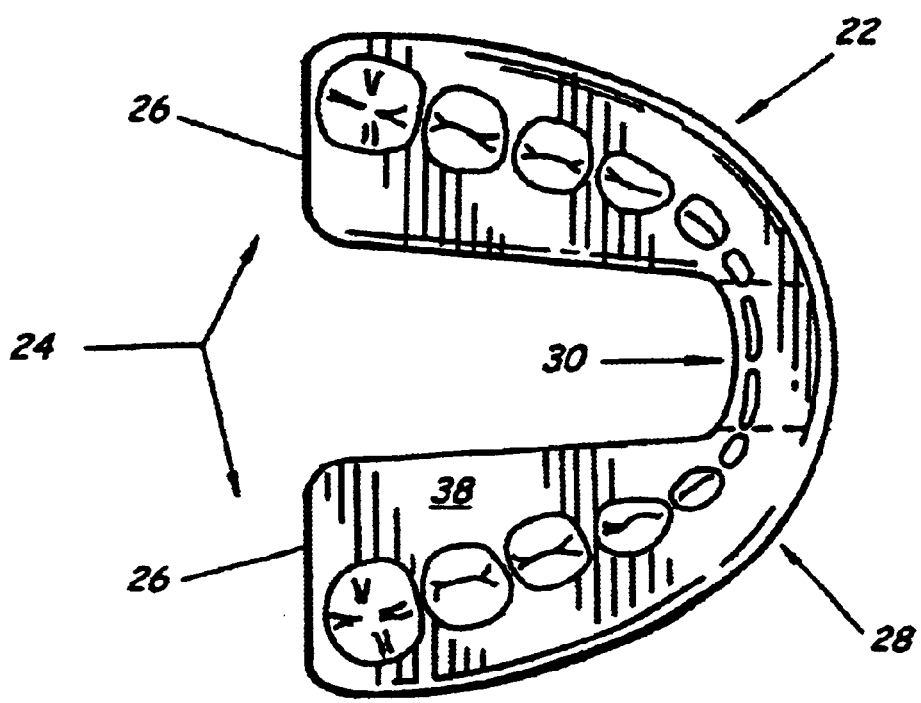
FIG. 4 is a top plan view of the inventive mouthpiece.
Figure 5:
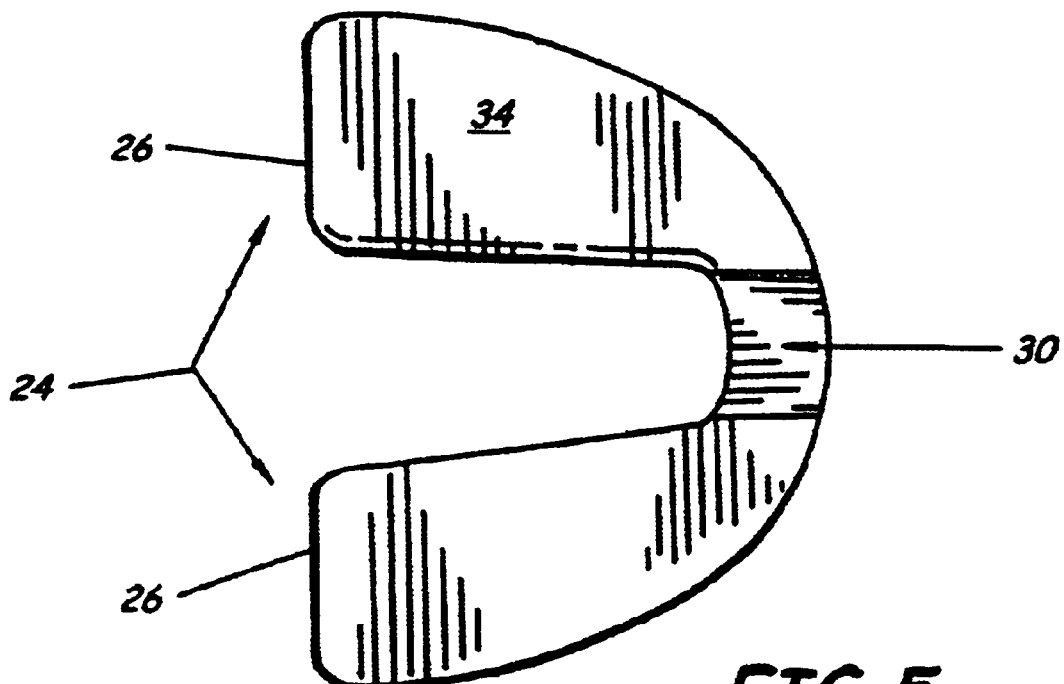
FIG. 5 is a bottom plan view of the mouthpiece of FIG. 4.
Figure 7:
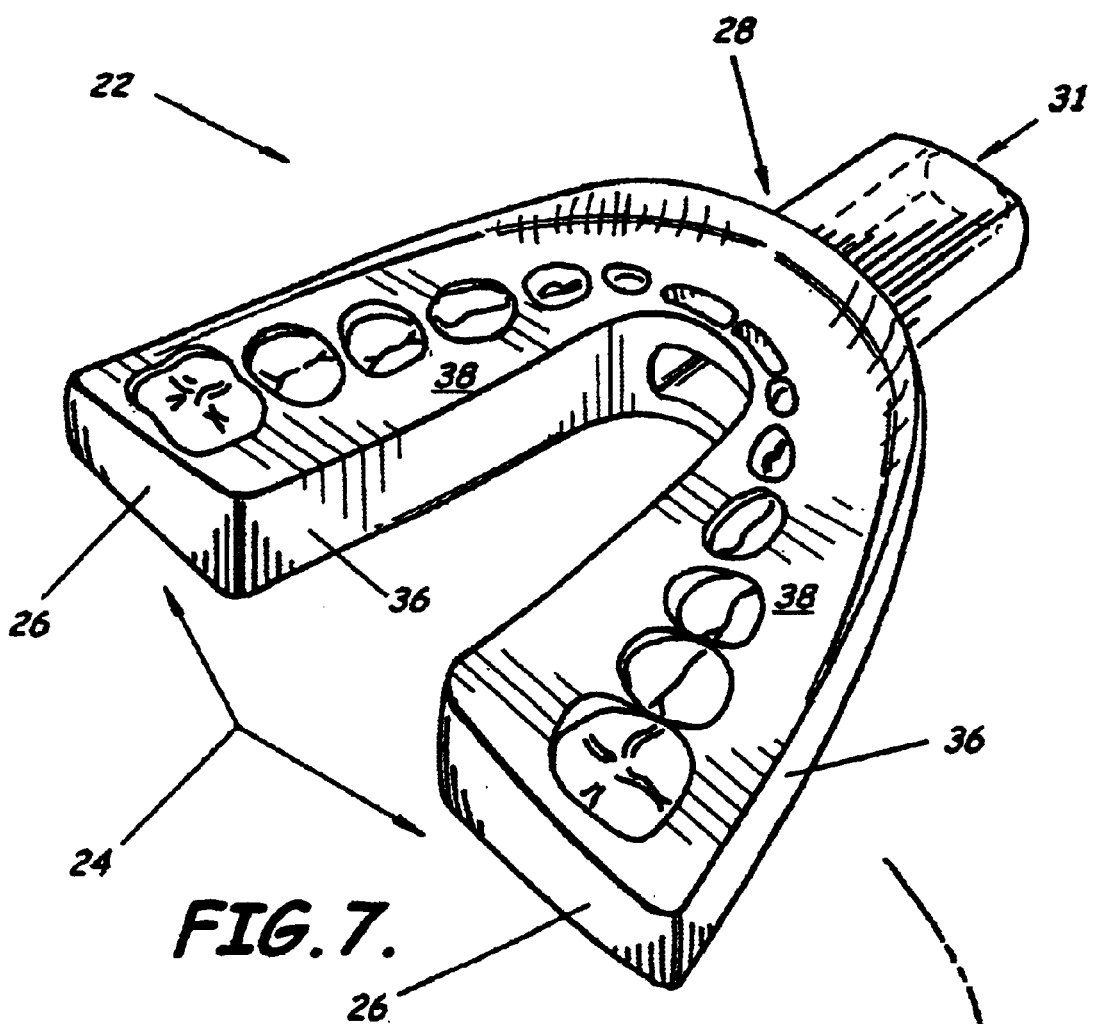
FIG. 7 shows another embodiment of the present mouthpiece.
Figure 8:
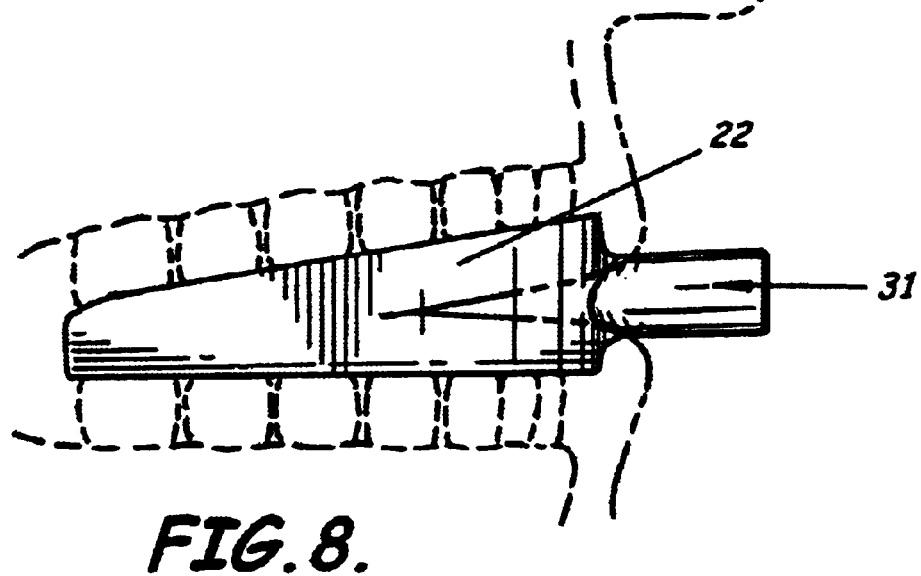
FIG. 8 is a cutaway lateral view showing the mouthpiece of FIG. 7 as worn by a user.
Figure 9:
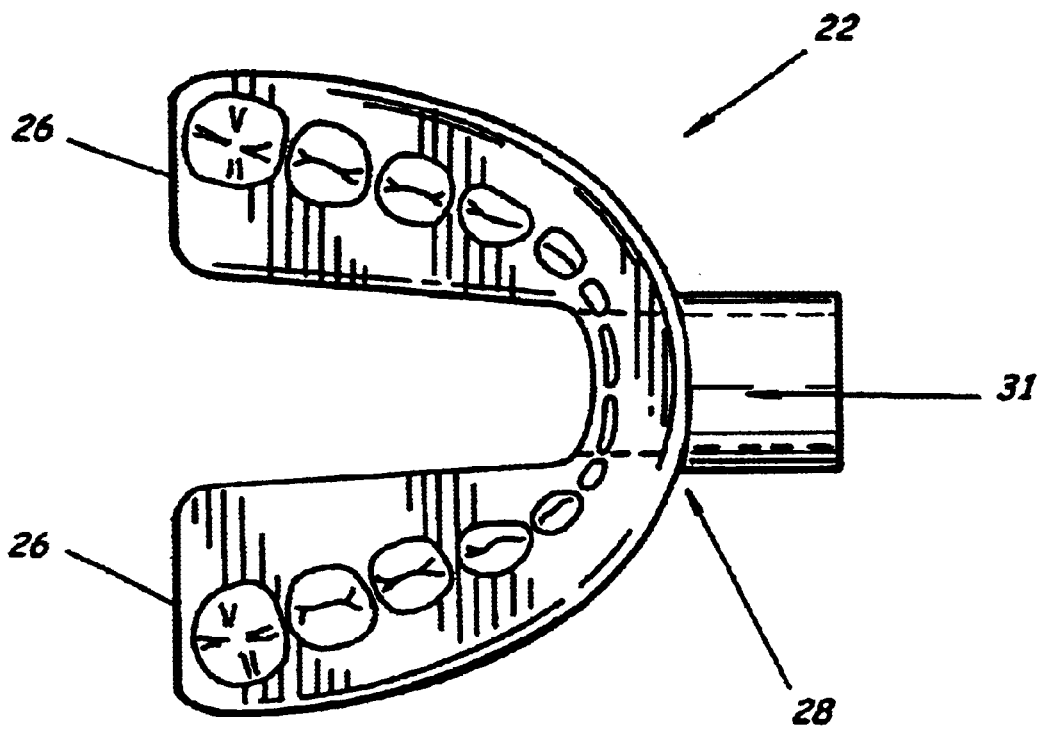
FIG. 9 is a top plan view of the mouthpiece of FIG. 7.
Figure 10:
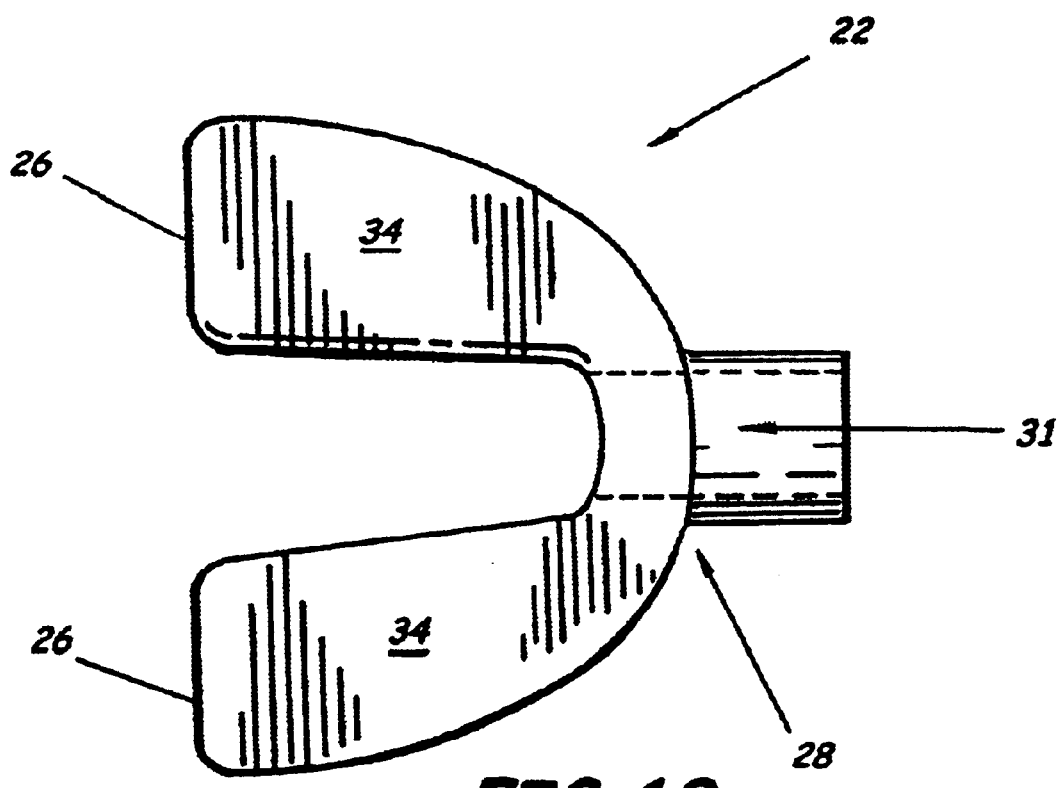
FIG. 10 is a bottom plan view of the mouthpiece of FIG. 9.
Figure 11:
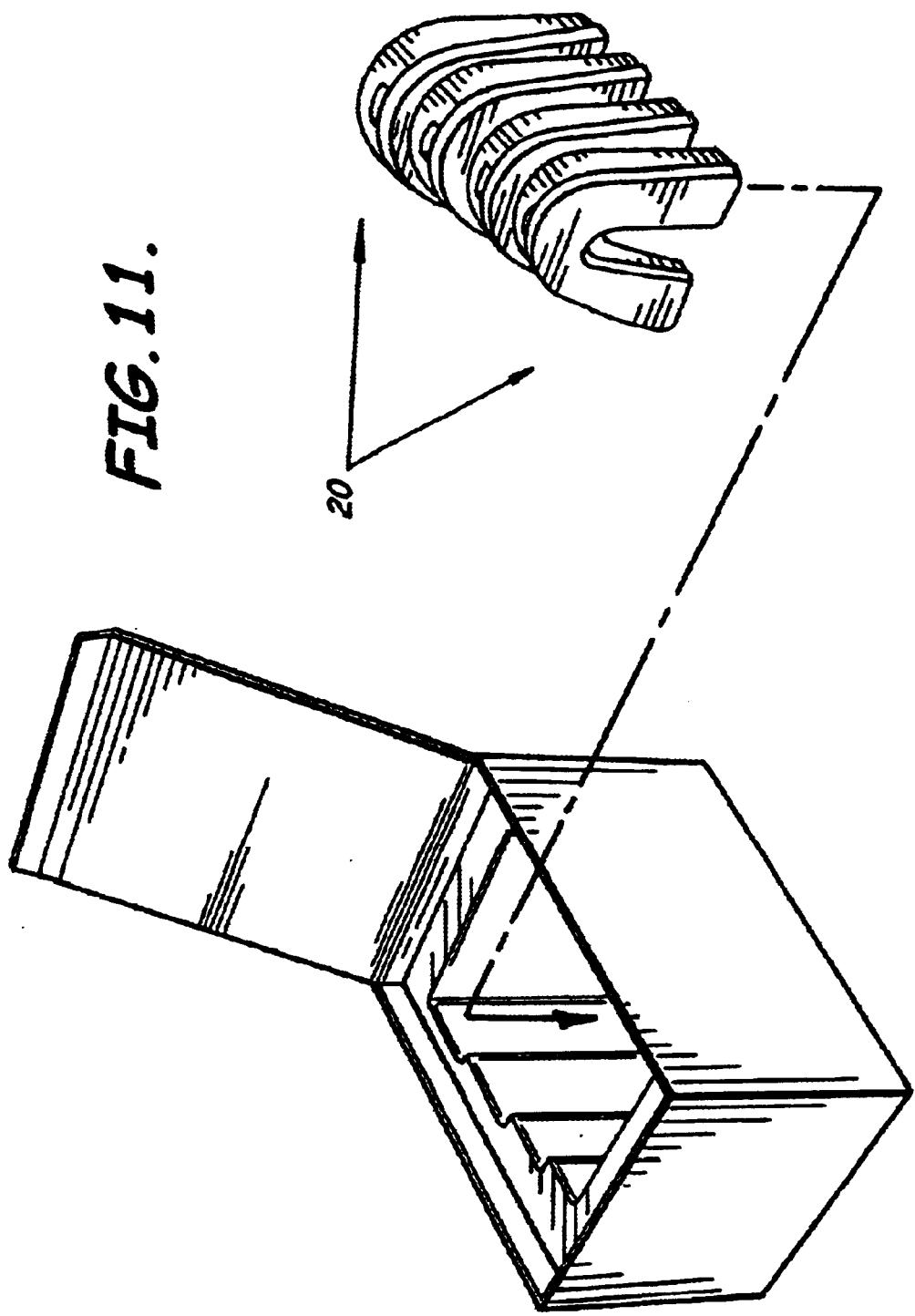
FIG. 11 illustrates a kit containing several of the mouthpieces of FIG. 1 as might be offered at retail.

The present mouthpiece 20 is preferably provided for retail sale in at least three general sizes, small, medium, and large, to custom fit a wide range persons having differently sized mouths. A typical retail kit 21 for sale of the mouthpiece 20 is shown in FIG. 11. Partly for the purpose of custom fitting, the mouthpiece body 22 has a lower surface 34 and an upper surface 38 spaced apart therefrom at an angle "α" which increases from the posterior end 24 to the anterior end 28 of said mouthpiece body. As best shown in FIG. 3, and also in FIGS. 6C, and 8, the angle of inclination "α" between the upper 38 and lower 34 surfaces of the mouthpiece body 22 is of importance in keeping the wearer's mouth and lips sufficiently open to allow unimpeded airflow through the anterior airway opening 30. An angle "α" of from about 10° to 20° has been found preferable, depending on the anterior-posterior overall length of the mouthpiece, which will somewhat vary from small to medium to large mouthpieces. Those skilled in the art will recognize, however, that angle "α" may be changed according to the size of the wearer's mouth, and that the range indicated above is given solely for purposes of illustration and not for limiting the invention.

Another embodiment of the present invention is shown in FIGS. 7–10, wherein the mouthpiece body 22 further comprises a tubular airway opening 31 extending outwardly from said anterior end airway opening 30. This embodiment of the mouthpiece body, best shown in use in FIG. 8, would be particularly useful for wearers having large, heavy, or especially protruding lips which might extend over the anterior end of the first embodiment of the mouthpiece as shown in FIGS. 1–6. The skilled will readily understand that it is important to keep the wearer's lips sufficiently spaced apart to maintain the proper function of the airway opening 30 at the anterior end of the mouthpiece.

Figure 12:
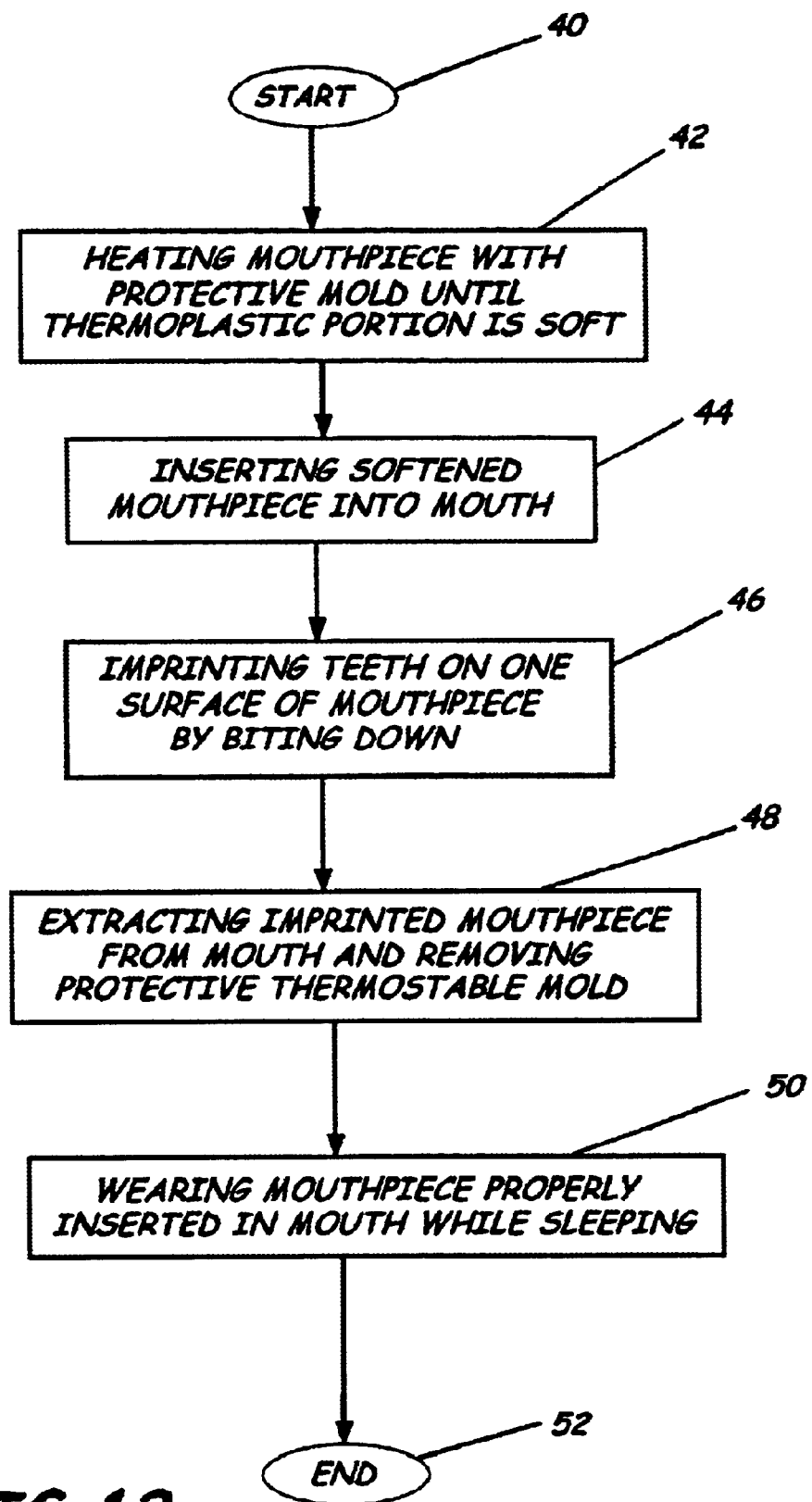
FIG. 12 shows a method of the invention of FIG. 1.

Method aspects of the present moutpiece invention are shown in FIG. 6 and FIG. 12, and include a method of reducing snoring during sleep. As shown in the block diagram of FIG. 12, the method starts 40 by heating 42 a mouthpiece body 22 made of a thermoplastic material and having a shape generally complementary to the person's dental arch. The mouthpiece body 22 includes a posterior end 24 having two spaced apart members 26 positioned toward the back of the person's dental arch when properly worn, and an anterior end 28 having an airway opening 30 therethrough, the anterior end positioned when properly worn to support the person's lips spaced apart so that air flows through the opening. The mouthpiece 20 further includes a substantially rigid protective mold 32 made of a thermostable material, the protective mold being complementary to said mouthpiece body. The protective mold 32 is removably engaged with the mouthpiece body 22 so that the mold protects at least lower and lateral peripheries of the mouthpiece body. Heating 42 of the mouthpiece body is preferably accomplished in a hot water bath and continues until the thermoplastic material has softened. When the mouthpiece 20 is cool enough, the method continues by inserting 44 the mouthpiece into the mouth of a person so that the mouthpiece is substantially aligned with the person's dental arch, and imprinting 46 the person's teeth along a surface of the mouthpiece body not protected by the mold 32 by biting down on the mouthpiece. The method then continues by extracting 48 the mouthpiece 20 from the person's mouth after imprinting, and removing the protective mold 32 from the mouthpiece body 22 after the mouthpiece body has cooled so as to reduce its plasticity. Finally, the method calls for wearing 50 the mouthpiece body 22 in the person's mouth during sleep, which when properly positioned the mouthpiece body is substantially aligned with the person's dental arch and is held between the teeth, so that the person's lips are supported by the anterior end 28 of the mouthpiece body 22 to allow the person to breathe through the airway opening 30 in the anterior end of the mouthpiece body. The method thereafter ends 52.

Those skilled in the art should understand that the protective mold 32 removably engaged with the mouthpiece body 22 will prevent teeth from imprinting along the lower surface 34 of the thermoplastic mouthpiece, thereby maintaining the lower surface relatively flat. The wearer's teeth will, however, imprint along the upper surface 38 of the mouthpiece, so as to provide a guide pattern for wearing the mouthpiece and to reduce slipping of the mouthpiece body 22 in the wearer's mouth. The relatively flat lower surface 34 of the mouthpiece body 22 helps in maintaining angle "α" in proper proportion, as it has been found that if the wearer imprints teeth along both upper 38 and lower 34 surfaces by biting down thereon, the angle "α" tends to be substantially reduced due to the depressions formed along both upper and lower surfaces of the mouthpiece. Imprinting teeth along only one surface reduces this possible variation at least in half, while still producing an easily wearable mouthpiece custom fitted to the wearer's dental arch. In addition, in a user who tends to grind her teeth while sleeping, the relatively flat lower surface 34 of the mouthpiece body 22 will allow the teeth to slide relative to the mouthpiece surface. If the lower surface 34 contained teeth imprints, the user's teeth would be substantially locked into their positions and a user grinding her teeth during sleep would experience added stress to the temporal-mandibular joint (also known as TMJ). Accordingly, the relatively flat lower surface of the present mouthpiece will also help alleviate such stress in the TMJ and neck area.

The skilled will readily understand that while the protective mold 32 has been described herein with respect to a lower surface 34 of the mouthpiece body 22, and imprinting has been described as occurring along the upper surface 38 of the mouthpiece, the wearer may prefer to turn the mouthpiece device upside down for imprinting. In such a case, the protective mold 32 would appear to engage an upper surface of the mouthpiece, and the teeth pattern would be imprinted along what might be described as a lower surface of the mouthpiece. Accordingly, the terms "upper" and "lower" are used herein to illustrate the invention for the skilled and are not intended to limit the invention to such an orientation. The inventive mouthpiece herein described is, therefore, usable in any applicable orientation, at the user's discretion or preference.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A mouthpiece for use by a person during sleep to aid in reducing snoring, said mouthpiece comprising:

a mouthpiece body of a thermoplastic material having a shape generally complementary to the person's dental arch, including a posterior end having two spaced apart members positioned toward the back of the person's dental arch when properly worn, and an anterior end having an airway opening therethrough, the anterior end positioned when properly worn to support the person's lips spaced apart so that air flows through the airway opening; and a substantially rigid, removable protective mold of a thermostable material, said protective mold complementary to said mouthpiece body and separably engaged therewith so that the mold protects at least lower and lateral peripheries of the mouthpiece body.

2. The mouthpiece of claim 1, wherein said mouthpiece body has a lower surface and an upper surface spaced apart therefrom at an angle which increases from the posterior end to the anterior end of said body.

3. The mouthpiece of claim 1, further comprising a plurality of moutpieces disposed in a container suitable for sale to the public as a kit.

4. A mouthpiece for use by a person during sleep to aid in reducing snoring, said mouthpiece comprising:
   a mouthpiece body of a thermoplastic material having a shape generally complementary to the person's dental arch, including a posterior end having two spaced apart members positioned toward the back of the person's dental arch when properly worn, and an anterior end, the anterior end positioned when properly worn to support the person's lips spaced apart so that air flows through the airway opening;
   an airway comprising a hollow member projecting outwardly from said anterior end, said hollow member having an airway opening therethrough; and
   a substantially rigid, removable protective mold of a thermostable material, said protective mold complementary to said mouthpiece body and separably engaged therewith so that the mold protects at least lower and lateral peripheries of the mouthpiece body.

5. The mouthpiece of claim 1, wherein said mouthpiece body has a lower surface and an upper surface spaced apart therefrom at an angle which increases from the posterior end to the anterior end of said body.

6. The mouthpiece of claim 1, further comprising a plurality of moutpieces disposed in a container suitable for sale to the public as a kit.

7. A method of reducing snoring during sleep, the method comprising:
   heating a mouthpiece body of a thermoplastic material having a shape generally complementary to the person's dental arch, including a posterior end having two spaced apart members positioned toward the back of the person's dental arch when properly worn, and an anterior end having an opening therethrough, the anterior end positioned when properly worn to support the person's lips spaced apart so that air flows through the opening, and having a substantially rigid, removable protective mold of a thermostable material, said mold complementary to said mouthpiece body and separably engaged therewith so that the mold protects at least lower and lateral peripheries of the mouthpiece body, wherein heating continues until the thermoplastic material has softened;
   inserting the mouthpiece into the mouth of a person so that the mouthpiece is substantially aligned with the person's dental arch;
   imprinting the person's teeth along a surface of the mouthpiece body not protected by the mold by biting down on the mouthpiece;
   extracting the mouthpiece from the person's mouth after imprinting, and removing the mold from the mouthpiece body after the mouthpiece body has cooled so as to reduce its plasticity;
   wearing the mouthpiece body in the person's mouth during sleep, wherein the mouthpiece body is substantially aligned with the person's dental arch and held between the teeth so that the person's lips are supported by the anterior end of the mouthpiece body to allow the person to breathe through the opening in the anterior end of the mouthpiece body.

8. A method of reducing snoring during sleep, the method comprising:
   heating a mouthpiece having a body of a thermoplastic material having a shape generally complementary to the person's dental arch, including an anterior end having an airway opening therethrough, the anterior end being sufficient to support the person's lips spaced apart so that air flows through the airway opening, and having a substantially rigid, removable protective mold of a thermostable material removably engaged with the mouthpiece body so that the mold protects at least portions of a lower surface of the mouthpiece body;
   imprinting the person's teeth along a surface of the mouthpiece body not protected by the protective mold;
   removing the protective mold from the mouthpiece body after the mouthpiece body has cooled;
   wearing the mouthpiece body properly aligned with the dental arch in the person's mouth during sleep.

* * * * *